United States Patent
Gleba et al.

(10) Patent No.: US 7,348,179 B2
(45) Date of Patent: Mar. 25, 2008

(54) IRES ENABLED GENE TRAPPING IN PLANTS

(75) Inventors: Yuri Gleba, München (DE); Newell Bascomb, Wayne, NJ (US); Mark Bossie, Robbinsville, NJ (US); Gerald Hall, Jr., Morrisville, PA (US); Thomas J. Petty, II, Ewing, NJ (US)

(73) Assignee: Icon Genetics, Inc., Princeton, NJ (US)

( * ) Notice: Subject to any disclaimer, the term of this patent is extended or adjusted under 35 U.S.C. 154(b) by 438 days.

(21) Appl. No.: 10/343,498

(22) PCT Filed: Apr. 17, 2002

(86) PCT No.: PCT/US02/11924

§ 371 (c)(1),
(2), (4) Date: Jun. 17, 2003

(87) PCT Pub. No.: WO02/083867

PCT Pub. Date: Oct. 24, 2002

(65) Prior Publication Data

US 2004/0014216 A1 Jan. 22, 2004

Related U.S. Application Data

(60) Provisional application No. 60/284,239, filed on Apr. 17, 2001.

(51) Int. Cl.
*C12N 15/82* (2006.01)
*C12N 5/14* (2006.01)
*C12N 5/04* (2006.01)
*A01H 5/00* (2006.01)

(52) U.S. Cl. .................... 435/468; 435/419; 435/320.1; 800/278; 800/295

(58) Field of Classification Search .................... None
See application file for complete search history.

(56) References Cited

FOREIGN PATENT DOCUMENTS

| WO | WO-98/54342 | 12/1998 |
|----|-------------|---------|
| WO | WO-98/55636 | 12/1998 |

OTHER PUBLICATIONS

Kerbach et al. (TGG, 111: 1608-1616, 2005).*
Urwin et al. (The Plant Journal, 24:583-589, 2000).*
Coppoolse et al. (Plant Mol. Biol., 51:263-279, 2003).*
Choi et al. (Nucleic Acids Research, 28:I-VII, 2000).*
Skulachev, et. al. "Internal Initiation of Translation Directed by the 5'-Untranslated Region of the Tobamovirus Subgenomic RNA I(2)" Virology, 1999, vol. 263, pp. 139-154.
Ivanov, et. al. "A Tobamovirus Genome That Contains an Internal Ribosome Entry Site Functional in Vitro." Virology, 1997, vol. 232, No. 1, pp. 32-43.
Toth, et. al. "A novel strategy for the expression of foreign genes from plant virus vectors." FEBS Letters, Jan. 2001, vol. 489. No. 2-3. pp. 215-219.
Nathalie Hardouin and Andras Nagy; "Gene-Trap-Based Target Site for Cre-Mediated Transgenic Insertion"; INSERM, Genesis 26:245-252 Wiley-Liss (2000).

* cited by examiner

*Primary Examiner*—Phuong T. Bui
*Assistant Examiner*—Vinod Kumar
(74) *Attorney, Agent, or Firm*—Lerner, David, Littenberg, Krumholz & Mentlik, LLP

(57) ABSTRACT

Disclosed are methods for introducing nucleic acid constructs called "landing pads" in plant genes for the insertion of transgenes, and methods for introducing the transgenes into the landing pads. Transgenic plants and plant parts produced by the methods, and seeds derived from the plants, are also disclosed.

12 Claims, 7 Drawing Sheets

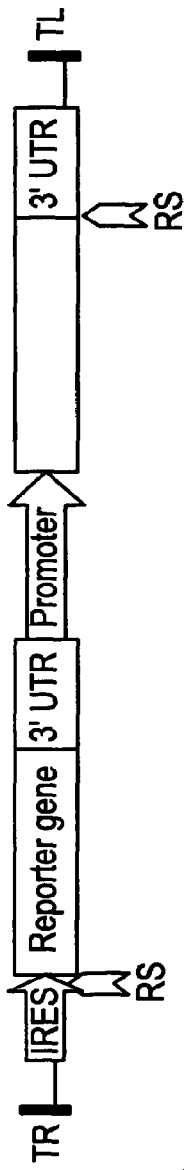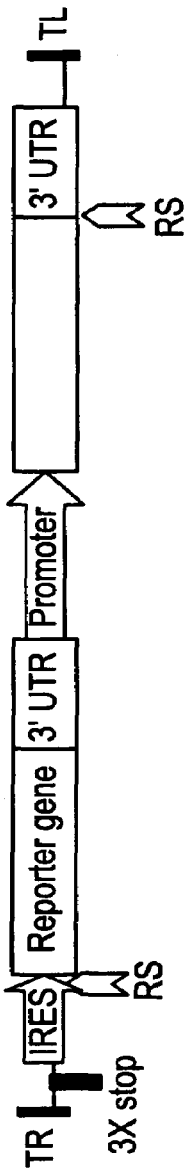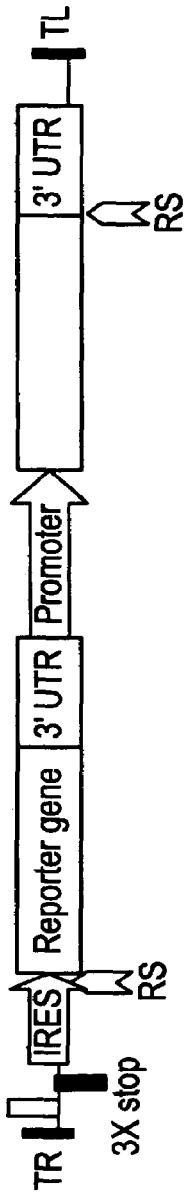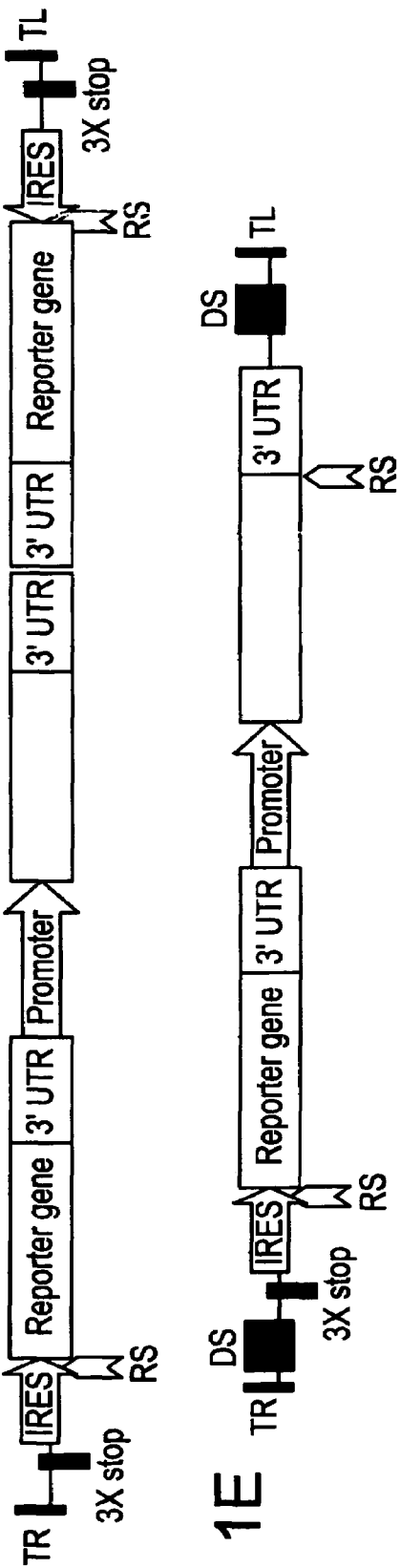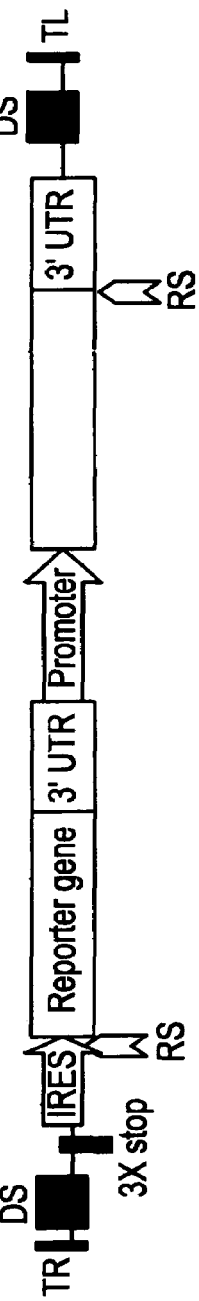
FIG. 1A
FIG. 1B
FIG. 1C
FIG. 1D
FIG. 1E

SEQUENCE LISTING

<160> NUMBER OF SEQ ID NOS: 2

<210> SEQ ID NO 1
<211> LENGTH: 75
<212> TYPE: DNA
<213> ORGANISM: Crucifer tobacco mosaic virus

<400> SEQUENCE: 1

```
ttcgtttgct ttttgtagta taattaaata tttgtcagat aagagattgt ttagagattt    60
gttctttgtt tgata                                                     75
```

<210> SEQ ID NO 2
<211> LENGTH: 148
<212> TYPE: DNA
<213> ORGANISM: Crucifer tobacco mosaic virus

<400> SEQUENCE: 2

```
gaattcgtcg attcggttgc agcatttaaa gcggttgaca actttaaaag aaggaaaaag    60
aaggttgaag aaaagggtgt agtaagtaag tataagtaca gaccggagaa gtacgccggt   120
cctgattcgt ttaatttgaa agaagaaa                                      148
```

IRES ENABLED GENE TRAPPING IN PLANTS

CROSS REFERENCE TO RELATED APPLICATIONS

The present application is a national phase entry under 35 U.S.C. § 371 of International Application PCT/US02/11924, filed April 17, 2002, published in English, which claims benefit of U.S. Provisional Patent Applications 60/284,239, filed Apr. 17, 2001. The disclosures of all of said applications are incorporated by reference herein.

TECHNICAL FIELD

This invention relates to DNA vectors containing internal ribosome entry site sequences (IRES) functional in plants and uses of the vectors in plants.

BACKGROUND

The ongoing genomic sequencing project on a number of organisms has resulted in an enormous amount of sequence data being deposited in public databases (Schuler, et al., Science 274:540-546 (1996)). Analyzing these data using a variety of bioinformatics tools can result in assigning function or protein identification to a number of these genes. However, true biological function cannot be determined without biological data. In animals and in plants the most successful strategy has been to knock out gene function either randomly through saturation mutagenesis or the use of antisense technology to study phenotype one gene at a time. In these functional screens, mutagenic agents are used to produce a large number of organisms that are analyzed for the specific phenotype or metabolic profile. Matching phenotype with genetic lesion has identified many genes involved in development and metabolism. This approach has been carried out successfully in the fruit fly *Drosophila melanogaster* (Nusslein-Volhard et al., Nature 287:795-801 (1980)), the nematode *C. elegans* (Brenner, Genetics 77:71-94 (1974)), and in *Arabidopsis thaliana* (Mayer, et al., Nature 353:402-407 (1991)).

In the mouse, gene trapping has provided a powerful approach to recover and identify novel phenotypes (Brown, J Inherit Metab Dis 21:532-539 (1998)). Ideally, in the process of gene discovery, no assumption should be made about which genes or pathways should be disrupted or examined. This approach, however, has not proven successful over time. With mice, however, the situation has changed dramatically with the advent of embryonic stem (ES) cell lines and the means to generate and select genetic alterations (Evans et al., Nature 292:154-156 (1981)). ES cells can be maintained in culture as totipotent cells, that is, cells that can give rise to all types of differentiated cells under proper growth conditions. These cells can also be genetically altered with relative ease (Thomas et al., Cell 51:503-512 (1987)). Like the ES cells from mice, plant cells from many plants are totipotent and can be used in similar studies.

Assigning gene function by observation of phenotype due to disruption of a gene in the transformed plant is not always straightforward. When there are multiple copies of a gene in a gene family, the phenotype might not be immediately evident. By determining the spatial and temporal expression of the disrupted gene, further evidence is gained for assigning gene function. This is especially valuable when a simple phenotype is not evident or when relating more complex phenotypes to functions and development of the whole organism. In some instances no obvious phenotype may be discerned but spatial and temporal expression of the reporter may provide critical information for defining the function of that genetic locus. The reporter gene is able to provide much higher resolution than gene chips or Northern analysis for tissue specific expression.

Including additional functions to the gene-trapping vector can provide novel tools for gene expression. With recombination sites incorporated into the vector it is possible to insert a gene of interest at this defined location. This may be done in a fashion to simply insert a gene of interest next to, or to replace the reporter gene, or to permit multiple/tandem insertions and replacements. Analysis of expression patterns in phenotypically normal plants will provide "landing sites" for inserting a gene of interest to obtain a highly specific and well-defined pattern of expression. As there are numerous drawbacks to the current random nature of gene insertion during plant transformation, this approach offers significant advantages.

Gene Trapping

Alternative strategies for identifying gene function were explored in the early 1990s. The approach of "gene trapping" was investigated to screen libraries of random mutants. The principal of gene trapping is essentially the random insertion of a DNA vector and the ensuing disruption of endogenous structural genes. Further improvements to the approach was to include a reporter gene that could readily signal the presence of the vector DNA. The reporter gene mimics the expression of the endogenous gene while mutating the same locus (Evans et al., Trends Genet. 13:370-374 (1997)). Large libraries of clones with random integrations can be isolated and stored indefinitely for future analysis. By using PCR (polymerase chain reaction) the sequence of the "trapped" gene can be identified. This technique allows the identification of genes regardless of their level of expression in vivo (Frohman et al., Proc. Natl. Acad. Sci. USA 85:8998-9002 (1988)). The ability to mutate, identify phenotype, and analyze expression of a specific gene makes gene trapping a very attractive tool for functional genomics. Gene trapping has been used for disruption and identification of genes in mouse ES cells (Skarnes et al., Genes Dev. 6:903-918 (1992)), Zambrowicz, et al., Nature 392:608-611 (1998)), genes including those membrane and secreted proteins (Skarnes et al., Proc. Natl. Acad. Sci. USA 92:6592-6596 (1995)), genes activated in differentiated mouse ES cells (Salminen et al., Dev. Dyn. 212:326-333 (1998)), genes to respond to retinoic acid (Forrester et al., Proc. Natl. Acad. Sci. USA 93:1677-1682 (1996)), and genes that are important in the development of the mammalian nervous system (Stoykova et al., Dev. Dyn. 212:198-213 (1998)).

Design of Gene Trap Vectors

Trapping vectors fall into essentially two different categories. The "enhancer-trap" vectors must integrate near an enhancer that activates the reporter gene that is fused to a minimal promoter (Bellen et al., Genes Dev 3:1288-1300 (1989)). "Promoter trap" vectors have no 5' expression element in front of the reporter. Gene-trap vectors may contain a splice acceptor (SA) at the 5' end of the reporter gene resulting in the generation of fusion transcripts following integration into the intron of an actively transcribed gene (Skarnes et al., Genes Dev. 6:903-918 (1992), Forrester et al., Proc. Natl. Acad. Sci. USA 93:1677-1682 (1996), Brenner et al., Proc. Natl. Acad. Sci. USA 86:5517-5521 (1989), von Melchner et al., Genes Dev. 6:919-927 (1992), Wurst et al., Genetics 139:889-899 (1995)). For functional genomics a gene-trap vector must provide three minimal functions. It must have a suitable reporter gene for the analysis of gene expression, the "trap event" must mutate the endogenous gene, and the sequence of the trapped cDNA and genomic site of integration must be able to be determined. For use as a landing site, the gene-trap vector must have a suitable reporter that can be measured in all cell types and all stages of development, the insertion of the gene trap must not result in impairment of the plant, and the recombination system must still be functional following integration. Landing pads may also be used for functional genomics. In this respect, the landing pad sites are used to test the effects of the expression of a novel gene whether or not that gene comes from the same source or a heterologous source. The function of an encoded gene product can be determined from the effect of ectopic expression of the gene.

In mouse ES cells, the DNA can be introduced by electroporation or by retroviral vectors that provide higher transfection frequency and integrate as intact a single copy. Likewise in plants, electroporation or particle bombardment can be used while Agrobacterium transformation can be used to introduce low or single copy genes.

The earliest vectors were used in undifferentiated ES cells (Skarnes et al., Genes Dev. 6:903-918 (1992), Friedrich et al., Genes Dev. 5:1513-1523 (1991)). The first gene-trap vectors contained an SA site in front of a promoterless reporter gene such as lacZ (which encodes the enzyme beta-galactosidase; Skarnes et al., Genes Dev. 6:903-918 (1992)) or beta-geo (which is formed from the beta-galactosidase gene (beta-gal) and the neomycin-resistance gene (neo) and encodes a fusion protein (Friedrich et al., Genes Dev. 5:1513-1523 (1991))). The integration of the vector into the intron of an expressed gene in the correct orientation results in a fusion messenger RNA (mRNA) transcript. Subsequently an internal ribosome entry site (IRES) from the encephalomyocarditis virus was inserted between the SA site and reporter gene sequence (Chowdhury et al., Nucleic Acids Res. 25:1531-1536 (1997)). The IRES allows dicistronic translation so the reporter gene can be translated independent of being fused in-frame to the trapped gene. With this vector it is important to realize that the level of expression of the reporter gene is dependent on the rate of transcription from the trapped gene.

The next generation vectors did not incorporate a poly-A site to direct the addition of a poly-A tail at the end of the introduced marker gene. The signal was provided by the endogenous gene to produce a stable mRNA (Zambrowicz et al., Nature 392:608-611 (1998), Salminen et al., Dev. Dyn. 212:326-333 (1998)). Rather than trapping at the promoter, these vectors incorporated a promoter but relied on trapping at the 3' end. The advantage of this vector was that the 3' end of the gene was sometimes more useful for gene identification.

Gene Traps in Plants T-DNA

Since T-DNA has not been shown to insert with any specificity, it is possible to saturate the genome with T-DNA insertions (Azpiroz-Leehan et al., Trends Genet. 13:152-156 (1997)). Large collections of T-DNA insertions have been generated in *Arabidopsis* (Feldmann et al., Mol. Gen. Genet. 208:1-9 (1987); Bouchez et al., Acad. Sci. Ser. III Sci. Vie 316:1188-1193 (1993); Campisi et al., Plant J. 17:699-707 (1999); Krysan et al., Plant Cell 11:2283-2290 (1999); Weigel et al., Plant Physiol. 122:1003-1014 (2000)) and systematic efforts have been ongoing to use these collections for "reverse genetic" screens (McKinney et al., Plant J. 8:613-622 (1995); Winkler et al., Plant Physiol. 118:743-750 (1998); Krysan et al., Plant Cell 11:2283-2290 (1999)). This approach is limited to those plant species that can be transformed by Agrobacterium. Although Agrobacterium generally delivers low or single copy gene insertions into the genome, multiple T-DNA insertions can often occur in a single plant (Bechtold et al., Acad. Sci. Ser. III Sci. Vie 316:1194-1199 (1993); Lindsey et al., Transgenic Res. 2:33-247 (1993)). Multiple enhancer or gene trap reporter gene insertions can complicate interpretation of expression patterns. The generation of complex insertions including T-DNA repeats (direct or inverted orientations) as well as rearrangements of adjacent chromosome DNA can also be problematic in interpreting gene expression patterns (Ohba et al., Plant J. 7:157-164 (1995); Nacry et al. Genetics 149:641-650 (1998); Laufs et al., Plant J. 18:131-139 (1999)). In addition to the complex gene expression patterns, the subsequent molecular analyses are also complicated making it difficult to isolate the genes of interest. Enhancer, promoter, and gene trap reporter genes have been used in plants by a number of different groups. The expression of the reporter gene has been efficient whether the reporter gene was positioned at either the left or the right T-DNA border (Lindsey et al., Transgenic Res. 2:33-247 (1993), Campisi et al., Plant J. 17:699-707 (1999)).

Transposable Elements

Insertional mutagenesis is routinely performed using transposable elements. Heterologous elements have been utilized in species that do not have active or well-characterized transposable elements systems (see Osborne et al., Genetics 129:833-844 (1991) for review). The elements in the system are introduced by T-DNA-mediated transformation and mobilization occurs subsequently. In the absence of a transposase the inserted transposable elements are stable. However, the transposable elements can be selectively de-stabilized upon expression of a transposase. The selective re-mobilization can lead to revertants, which can then be used to verify that the phenotype was indeed caused by insertion of the transposon.

Behavior of the maize Ac/Ds and En/Spm transposable elements has been extensively studied in heterologous species. They have also been modified for efficient transposition in tobacco, tomato, and *Arabidopsis* (see Osborne et al., Curr. Opin. Cell Biol. 7:406-413 (1995) for review). The Ac/Ds system has been used for enhancer or gene trap systems to date. The Ac/Ds system has the advantage of low copy number, which is an advantage over the En/Spm system, which has a tendency to amplify (Aarts et al., Mol. Gen. Genet. 247:555-564 (1995)). The maize Mu element is being exploited for functional genomic studies in maize. Plant retrotransposons also can be used in this invention. Retrotransposons are widely distributed among eukaryotes including plants (Langdon et al., Genetics 156:313-325 (2000)). Some of them, like tobacco Tnt1 (Grandbastien et al., Nature 337:376-380 (1989); Feuerbach et al., J. Virology 71:4005-4015 (1997)) and Tto1 (Hiroshika et al., , Gene 165:229-232 (1995); Takeda et al., Plant J. 28:307-317 (2001)) are well studied and can be used for engineering technology described in this invention.

IRES Elements in Plants

According to the ribosome-scanning model, traditional for most eukaryotic mRNAs, the 40S ribosomal subunit binds to the 5'-cap and moves along the nontranslated 5'-sequence until it reaches an AUG codon (Kozak, Adv. Virus Res. 31:229-292 (1986); Kozak, J. Mol. Biol. 108: 229-241 (1989)). Although for the majority of eukaryotic mRNAs only the first open reading frame (ORF) is translationally active, there are different mechanisms by which mRNA may function polycistronically (Kozak, Adv. Virus Res. 31:229-292 (1986)).

In contrast to the majority of eukaryotic mRNAs, the initiation of translation of picornavirus RNAs takes place by an alternative mechanism of internal ribosome entry. A picornaviral 5'-nontranslated region (5'NTR) contains a so-called internal ribosome entry site (IRES) or ribosome landing pad (Pelletier et al., Nature 334:320-325 (1988); Molla et al., Nature 356:255-257 (1992)). Internal ribosome entry has also been reported for other viral (Le et al., Virology 198:405-411 (1994); Gramstat et al., Nucleic Acid Res. 22:3911-3917 (1994)) and cellular (Oh et al., Gen Dev. 6:1643-1653 (1992)) RNAs. It is important to emphasize that the picornavirus and other known IRESes are not active in the plant cell systems.

Recently a new tobamovirus, crTMV, has been isolated from *Oleracia officinalis* L. plants and the crTMV genome has been sequenced (6312 nucleotides) (Dorokhov et al., Doklady of Russian Academy of Sciences 332:518-522 (1993); Dorokhov et al., FEBS Lett. 350:5-8 (1994)). A peculiar feature of crTMV is its ability to infect systemically the members of Cruciferae family. The crTMV RNA contains four ORFs encoding the proteins of 122K (ORF1), 178K (ORF2), the read-through product of 122K, 30K MP (ORF3) and 17K CP (ORF4). Unlike other tobamoviruses, the coding regions of the MP and CP genes of crTMV overlap for 25 codons, i.e. 5' of the CP coding region are sequences encoding MP.

It has been shown that unlike the RNA of typical tobamoviruses, translation of the 3'-proximal CP gene of crTMV RNA occurs in vitro and in planta by the mechanism of internal ribosome entry that is mediated by a specific sequence element, $IRES_{cP148}$ (Ivanov et al., Virology 232: 32-43 (1997)). The results indicated that the 148-nt region upstream of the CP gene of crTMV RNA contained $IRES_{CP148}$ promoting internal initiation of translation in vitro and in vivo (protoplasts and transgenic plants).

Recently it has been shown (Skulachev et al., Virology 263:139-154 (1999)) that the genomic RNAs of tobamoviruses contain a region upstream of the MP gene that are able to promote expression of the 3'-proximal genes from chimeric mRNAs in a cap-independent manner in vitro. The 228-nt sequence upstream from the MP gene of crTMV RNA ($IRES_{MP228}^{CR}$) mediates translation of the 3'-proximal GUS gene from bicistronic transcripts. It has been shown that the 75-nt region upstream of the MP gene of crTMV RNA is still as efficient as the 228-nt sequence. Therefore the 75-nt sequence contains an $IRES_{MP}$ element ($IRES_{MP75}^{CR}$). It has been found that in similarity to crTMV RNA, the 75-nt sequence upstream of genomic RNA of a type member of tobamovirus group (TMV UI) also contains $IRES_{MP75}^{UI}$ element capable of mediating cap-independent translation of the 3'-proximal genes in RRL and WGE.

On the whole the data prove unambiguously that the 228-and 75-nt sequences upstream of MP gene derived from genomic RNAs of different tobamoviruses contain a new IRES element ($IRES_{MP}$). Efficiency of $IRES_{MP}$ in internal translation was similar to that of $IRES_{CP}$.

The tobamoviruses provide a new example of internal initiation of translation, which is markedly distinct from IRESes shown for picornaviruses and other viral and eukaryotic mRNAs.

In patent application (PCT/FI98/00457) it has been shown that tobamoviruses IRES elements provide an internal translational pathway of the 3'-proximal gene expression from bicistronic chimeric RNA transcripts in plant, animal, human and yeast cells. These RNA sequence elements situated upstream of movement protein (MP) and coat protein (CP) genes, are designated respectively as an internal ribosome entry site of MP ($IRES_{MP}$) and CP ($IRES_{CP}$) genes, respectively. Both IRESes can be employed to produce chimeric bi- or multicistronic mRNAs for co-expression of heterologous (or multiple homologous) genes in plant, animal, human and yeast cells, and also transgenic plants and animals. The efficient (more than 30% in comparison to monocistronic transcript) $IRES_{MP}$- and $IRES_{CP}$-mediated expression of the second (3') foreign gene from bicistronic transcript was demonstrated in plants transgenic for bicistronic constructs, in transient expression assays (on electroporated protoplasts or in particle bombardment experiments) and in vitro in cell-free protein synthesizing systems of plant (wheat germ extracts) or animal (rabbit reticulocyte lysates) origin; in human (HeLa) cells transformed with bicistronic $IRES_{MP}$-containing constructs and in yeast cells transformed with the said bicistronic constructs. The $IRES_{MP}$ element capable of mediating cap-independent translation is contained not only in crTMV RNA but also in the genome of a type member of tobamovirus group, TMV UI, and another tobamovirus, cucumber green mottle mosaic virus. Consequently, different members of tobamovirus group contain $IRES_{MP}$.

SUMMARY OF THE INVENTION

The present invention utilizes IRES elements active in plants to identify structural genes in the plant genome and to create landing pads in the plant genome for the introduction of nucleic acids of interest.

One aspect of the present invention provides for a method of using IRES-based vectors for identifying and characterizing transcriptionally active regions in plants based on insertional inactivation of the resident gene at the integration site. This method entails randomly inserting into a plant genome an IRES construct or vector that contains an IRES element linked to a reporter gene. The IRES increases the efficiency the gene of interest to be expressed in the same temporal and spatial manner as the resident gene into which it is inserted, thus avoiding the necessity of inserting the GOI precisely into the 5' untranslated region or in correct reading frame. The reporter gene is expressed (and thus detected) only if the IRES vector is inserted into a structural gene within the plant genome. Thus, integration of the IRES vector into non-coding regions of the plant genome does not result in a detectable signal.

An advantage of the present method is that the IRES vector does not have to integrate into the structural gene in proper reading frame in order for the reporter gene to be expressed. In addition, the method provides further information with respect to the expression patterns of the gene into which the IRES vector is inserted. Specifically, detection of the reporter gene in a certain plant part and/or at a particular time during the development of the plant indicates that the structural gene is expressed in this particular plant part and/or the particular time during plant development. The IRES vector also functions as a physical tag in the sense that the IRES vector can be extracted along with the plant DNA that flanks it, which in turn will provide an identification and function of the structural gene into which the IRES vector was inserted. Transformed plants, plant parts, plant cells and protoplasts produced by these processes, and seeds derived from the plants, are also provided.

In preferred embodiments, the vector also contains a 3' untranslated region containing a transcriptional stop signal and/or a polyadenylation site. The vector may also contain an independent transcription unit containing a promoter, selectable marker and a terminator. The vector may also contain stop codons in all three reading frames upstream of the IRES, or a splice acceptor site upstream of the IRES or the stop codons. The vector may contain a second IRES driven marker gene in a convergent orientation such that the two transcription units are on ends of the vector. The construct or vector may be flanked by transposon inverted repeats.

Another aspect of the present invention provides for a method of using IRES constructs or vectors to generate defined landing pads for the integration of DNA sequences into the plant. The sites of the landing pads may be determined in accordance with the first aspect of the present invention such as by identifying a structural gene within the plant genome that is expressed in a certain plant part and/or during a particular time during the development of the plant. The integration of the new DNA sequence, e.g., a structural gene that is native or non-native to the plant, is introduced into the plant genome at the particular landing pad site. The landing pad sites provide the desired temporal and or spatial expression of a newly introduced gene by virtue of placing it in proper register with the IRES element active in plants at a particular locus of transcriptional activity. The landing pad site contains in addition to the IRES element and the reporter gene, one or more site-specific recombination sites. The nucleic acid of interest to be introduced into the site is associated with one or more site-specific recombination sequences. The nucleic acid of interest can be, but not limited to, any gene providing for useful trait, which has to be expressed in a desired temporal and or spatial manner. The plant or plant part containing the landing pad site is transformed with the nucleic acid. A recombinase, an enzyme that catalyzes the introduction of the nucleic acid into the site, may be provided recombinantly in the same or a companion vector with the nucleic acid of interest in either a stable or transient fashion. A preferred recombinase is the integrase from bacteriophage Phi C31. Thus, the compositional nature of the construct containing the DNA to be introduced into the plant genome depends on the format of the landing pad and whether the recombinase is already present in the plant. Preferred methods for introducing the construct into the landing pad include DNA transformation, viral transfection and plant crossing. Transformed plants, plant parts, plant cells and protoplasts produced by these processes, and seeds derived from the plants, are also provided.

Yet another aspect of the present invention is directed to a method of using a variety of landing pad lines to deliberately miss-express DNA sequences of unknown function to discern their function based on ectopic gene expression. In this aspect of the invention, transformants having landing pad sites within a structural gene in the genome that has been determined to be expressed in certain plant part(s) and/or at certain time(s) of development, are further transformed with the nucleic acid of unknown function. Changes in phenotype are observed and correlated with function of the unknown nucleic acid. Transgenic or transformed plants, plant parts, plant cells and protoplasts produced by these processes, and seeds derived from the transformed plants, are also provided. The constructs e.g., vectors, used to transform the plant cells are further provided.

BRIEF DESCRIPTION OF THE DRAWINGS

FIGS. 1a-e are schematic presentations of different versions of a "gene trap" vector.

BEST MODE OF CARRYING OUT THE INVENTION

Figure 2:
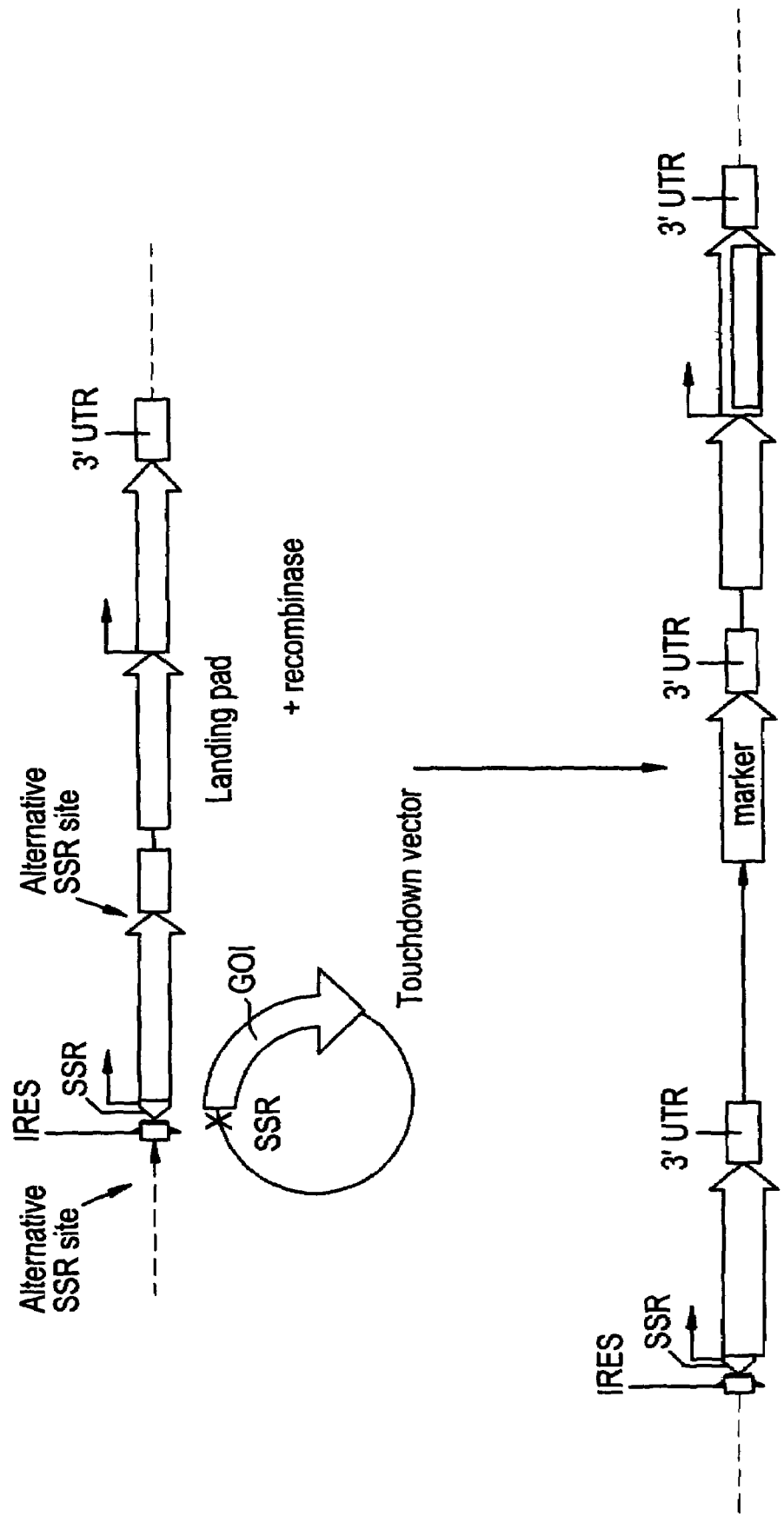
FIG. 2 is a schematic diagram depicting the constructs designed for cloning any GOI in order to incorporate into the "landing pad" by integration.

This invention describes plasmid constructs containing novel internal ribosome entry site sequences (IRES) functional in plants linked to a marker gene and uses for plant functional genomics, genetic regulatory element identification and isolation, and genetically engineered genomic receptor sites (landing pads) for introduction and expression of new genes. The IRES-based gene tagging and landing pad vectors are DNA constructs that can be inserted into genomic DNA of a host organism allowing for the expression of a marker gene or gene of interest relying on transcriptional regulation of the native genetic locus rather than ectopic regulatory elements such as promoters and enhancers. Initiation of translation of the introduced gene is cap site independent.

Gene element trapping vectors (e.g., plasmids) are constructs designed to identify genomic regulatory elements and genes based on the vector insertion into actively transcribed host DNA sequences. Minimally these would include an IRES and a reporter gene or an IRES and reporter gene along with a selectable gene.

Genomic landing pad vectors are similar to gene element trapping vectors with additional elements to allow insertion of a gene of interest (GOI) or replacement of a marker gene with a GOI via site-specific or homologous recombination.

"Touchdown vectors" are vector (e.g., plasmid) constructs carrying the GOI and appropriate elements (e.g., cognate site-specific recombination sites) for incorporation into a genomic landing pad. These vectors contain no transcriptional regulatory sequences associated with the GOI, relying upon the regulatory sequences at the site of genomic insertion for expression.

An IRES (internal ribosome entry site) is a nucleic acid sequence capable of initiating translation at internal start codons along an RNA (messenger RNA). The IRES functions independently of the mRNA cap and/or ribosome scanning. These are used in the present invention to permit expression of a marker gene to allow analysis of expression patterns of the genomic transcripts in which it has been introduced. Any sequence functional in plants, regardless of origin, that allows translation at internal start codons independent of a 5' cap or ribosome scanning is considered an IRES for purposes of the present invention. Thus, IRESes of various origins, including plants, viruses and synthetic preparation may be used.

By way of example, two specific IRES elements are derived from the genome of the crucifer tobacco mosaic virus (crTMV):IRESmp75$^{cr}$: TTCGTTTGCTTTTTGTAG-TATAATTAAATATTTGTCAGATAAGAGATTGTTTAG-AG ATTTGT TCTTTGTTTGATA (SEQ ID NO: 1) IREScp148$^{cr}$: GAATTCGTCGATTCGGTTGCAGCATT-TAAAGCGGTTGACAACTTTAAAAGAAGGA AAAA-GAA GGTTGAAGAAAAGGGTGTAGTAAGTAAG-TATAAGTACAGACCGGAGAAGTACGC CGGTCCTG ATTCGTTTAATTTGAAAGAAGAAA (SEQ II) NO: 2)

Marker genes encode proteins that cause an observable or measurable phenotype such that gene expression can be discerned from lack of or varying levels of expression. Marker genes may include reporter genes, yielding a visual calorimetric, fluorescent, luminescent or biochemically assayable product; selectable markers, allowing for selection of transformants based on physiology and growth differential; or other genes displaying a visual physiologic or biochemical trait. Common examples of reporter genes include lacZ (β-galactocidase), GUS (β-glucuronidase), GFP (green fluorescent protein), luciferase, or CAT (chloramphenicol acetyltransferase), which are easily visualized or assayable. Selectable markers, such as antibiotic (kanamycin or hygromycin) resistance, herbicide (glufosinate, imidazolinone or glyphosate) resistance or physiological markers (visible or biochemical) have the advantage of selecting only the cells expressing the protein but are not easily quantifiable.

Gene of interest (GOI) or structural GOI refers to any gene(s) (protein coding region), sense or antisense, of a gene to be inserted and expressed in the host plant. This could be a host gene or heterologous gene from another organism that requires over-expression, alternative expression patterns, gene silencing via homology dependent silencing or antisense RNA. The GOI may also include mutated or engineered natural genes. GOIs are not limited to agronomically significant genes. A GOI may express a pharmaceutically valuable protein, for example. Thus, the GOI is any nucleic acid that is expressible in a plant.

Site-specific recombinase systems have been well documented in bacteriophage and integrative plasmids. These systems have been extensively studied and adapted for use in transgene integration and chromosomal engineering in plants and animals. The site-specific recombination systems require the expression of one or more recombinase or integrase proteins and the presence of two sites recognized by the recombinase. The recombinases recognize the specific sites and cause recombination between two sites in cis or trans. Recombinases can cause exchange, insertion, excision or inversion depending upon the relative location and orientation of the recombination sites to each other. Exchange occurs when the sites are on different linear fragments of DNA. If at least one of the substrate DNAs is circular, integration will occur. When the recombination sites are on the same DNA fragment excision occurs if these sites are in the same orientation but causes inversion if the orientations are in opposite orientations. Thus, depending upon the application, topology as well as orientation of the recognition sites is critical. This makes the site-specific recombinases very amenable to genome engineering due to the very precise nature of the integration. Site-specific recombination systems may be based on the λ integrase family of recombinases (λ recombinase from bacteriophage Lambda, CRE-lox from bacteriophage P1, FLP-FRT from *Saccharomyces cerevisiae*, R-RS system of *Zygosaccharomyces rouxii* and the Gin-gix system of bacteriophage Mu) or the resolvase/invertase family (C31 integrase from bacteriophage ΦC31). Examples of suitable site-specific recombination systems for use in the present invention are disclosed in the literature, including the cre-lox system (Sauer, U.S. Pat. No. 4,959,317, Odell, et al., U.S. Pat. No. 5,658,772; Odell, et al., PCT WO91/09957) and the FLP-FRT system (Hodges and Lyznik, U.S. Pat. No. 5,527,695).

Site-specific recombinases from bacteriophage and yeasts are being widely used as tools for manipulating DNA both in the test-tube and in living organisms. Preferred recombinases/recombination site combinations for use in the present invention are cre-lox, FLP-FRT, ΦC31 and R-RS. Other suitable systems include the intron-encoded yeast endonuclease I-SceI, may be used. See, Choulika et al., Mol. Cell Biol. 15:1968-1973 (1995). Regardless of whether recombination sites are placed on or within a single DNA molecule in direct or opposite orientation, or placed on unlinked linear or circular DNA molecules, the corresponding recombinase can catalyze the reciprocal exchange to produce a deletion, inversion, translocation or co-integration event. See, Bollag et al., Ann. Rev. Genet. 23:199-225 (1989); Kilby et al., Trends Genet. 9:413-421 (1993); and Ow, Curr. Opinion Biotech. 7:181-186 (1996).

In the present invention, recombinase-mediated site-specific translocation occurs between an introduced DNA and a landing site in a gene of interest on a chromosome, wherein the resident gene may be selected based on spatial and/or temporal expression pattern. This in-trans recombinase effect is essential in order to effect transfer of transgenes between an exogenous DNA molecule and a chromosome. See, Dale et al., Gene 91:79-85 (1990); Odell et al., Mol. Gen. Genet. 223:369-378 (1990); Dale et al., Proc. Natl. Acad. Sci. USA 88:10558-10562 (1991); Russell et al., Mol. Gen. Genet. 234:49-59 (1992); Lyznik et al., Plant J. 8:177-186 (1995); Albert et al., Plant J. 7:649-659 (1995); van Deuersen et al., Proc. Natl. Acad. Sci. USA 92:7376-7380 (1995).

One particular utility of known recombination systems for transgene management in plants is directed excision of a transgene from plant genome, a procedure that allows elimination of unwanted heterologous genetic material such as antibiotic selective markers from a commercial variety (Ow et al., PCT WO93/01283). These systems, however, address an entirely different utility area, namely, the use of site-specific recombination to eliminate unwanted portions of heterologous DNA, rather than to manage separation of flows of transgenes and resident plant genes. Another utility is described in Hooykaas and Mozo, U.S. Pat. No. 5,635,381, and Offringa et al., U.S. Pat. No. 5,501,967, directed to the use of site-specific recombination systems to achieve a site-directed targeted integration of DNA into plant genomes via Agrobacterium-mediated transformation.

The site-specific recombination techniques and IRES elements utilized by the present invention have clear and strong advantages. By employing precise targeting via homology-addressed DNA sites, transgene "landing sites" can be created that are carefully selected and characterized in advance. As a result, higher level of predictability and reproducibility of transgene behavior, including heritability, expression level, absence of silencing, etc., is achieved. Also, later versions of the transgene cassette can be addressed to the same site, replacing old versions of transgenes with newer ones. Subsequent breeding of the material with a pre-selected and determined and mapped integration sites is much easier and relatively straightforward. The IRES increases the efficiency the gene of interest to be expressed in the same temporal and spatial manner as the resident gene into which it is inserted, thus avoiding the necessity of inserting the GOI precisely into the 5' untranslated region or in correct reading frame.

Splice acceptor (SA) includes a 3' intron splicing site and branch site which may be added to the constructs to allow expression from genomic insertions within an endogenous intron. A branch site and splicing acceptor site may be placed 5' of the expression cassette such that insertion of the construct into an intron allows the formation of a fusion transcript using the endogenous splicing donor.

Transposons are naturally occurring mobile genetic elements, especially prevalent in many plant species, which have the ability to move, jump or re-locate within the genome. Several transposons, such as Ac/Ds, En/Spm have been cloned and are well characterized as genetic tools in heterologous plant species. Mu is being exploited as a genetic tool in maize. Two components, very similar to most recombinases, are required for transposition. First, is the expression of the transposase enzyme, and second is the presence of inverted terminal repeats recognized by the transposase enzyme. The major difference between recombinases and transposases is that transposition occurs at random sites in the genome making them useful for mutational analysis. Furthermore, the transposons can be induced to excise again to obtain revertants or "gain of function". This is useful information when trying to establish a function of the mutated gene. Genetic element/gene trapping and functional knockouts Many of the limitations of classical gene trapping vectors can be overcome if translation of the marker gene does not rely on the use of capped mRNA or fusion proteins. Accordingly, in one aspect of the present invention, internal ribosome entry sites (IRES) are used with a marker gene to permit analysis of expression of the transcripts in which it has been introduced. The IRES is placed immediately upstream of the marker gene-coding region such that insertion anywhere in a transcribed region of the plant genome yields a fusion transcript. In the absence of an IRES element, expression is dependent on insertion into the 5' untranslated region or correct in-frame insertion into an exon. The presence of the IRES allows for translation of a "non-fused" reporter protein at the internal site allowing translation of a non-fusion protein regardless of the insertion point within the endogenous exon. Because reading frame and insertion point dependency are eliminated, there is a dramatic increase in the number of inserts within transcribed regions that yield useful information through a functional reporter gene product. With a greater number of "hits" more useful genomic locations are identified.

The gene element trapping vectors are constructs designed to identify genomic regulatory elements and genes based on their insertion into actively transcribed host DNA sequences. In their most basic form, the gene tagging vectors contain an IRES element upstream of a marker gene. In a preferred embodiment, the vector includes a 3' untranslated region for more efficient processing of the transcript (FIG. 1a). The preferred marker genes are reporter genes that provide a visible signal, such as β-glucuronidase (GUS), green fluorescent protein (GFP) or luciferase (LUC). The presence of a reporter gene allows for direct analysis of the transcriptional activity of the genomic site of insertion. In a less preferred embodiment, the marker gene is a selectable marker, because it causes limitations based on the type of selection. For example, transformants are typically selected based on constitutive expression of the selectable marker gene in the appropriate tissue to protect the transformed cells from the selection pressure of antibiotics, herbicides or selective growth conditions. The placement of such a gene under the control of the genomic regulatory sequences would limit the number of productive insertions to those that produce an appropriate level, temporal and spatial expression pattern of the selectable marker gene. Thus it is preferable to use the selectable marker genes for transformation and regeneration driven by an independent constitutive promoter. Other genes exhibiting a scorable phenotype may also be used as marker genes to identify and analyze tagged genes and genomic elements.

Although not specifically required, selectable markers under the control of an independent, constitutive promoter may be included in the gene trapping constructs. This allows for selection of transformed cells that are regenerated into plants and subsequently screened for a wide variety of marker gene expression profiles.

In addition to the foregoing, the vector constructs may further contain the following elements depending upon the application.

Stop codons may be inserted in all thre reading frames upstream of the IRES in order to terminate translation from the natural open reading frame to insure efficient translation from the IRES and elimination of potential fusion protein products (FIG. 1b).

A Splice acceptor (SA) may be added to the constructs to allow expression from insertions into an intron. Normally the vector sequences are removed during mRNA processing with the rest of the intron. However, inclusion of a branch site and 3' splicing site placed at the 5' end of the expression cassette allows the formation of a fusion transcript using the endogenous splicing donor (see FIG. 1c).

The IRES/marker construct may be placed at the right or left border of the T-DNA, or both. Placing two IRES elements each driving a different marker in convergent directions on the ends of the T-DNA allows expression of one or the other genes depending on orientation (see FIG. 1d).

Transposons may also be a useful addition to the gene element tagging system. Transposons are naturally occurring mobile genetic elements, especially prevalent in many plant species, which have the ability to move, jump or re-locate within the genome. Several transposons, such as Ac/Ds, Mu, and En/Spm, have been cloned and are well characterized as genetic tools in heterologous plant species. Two components, very similar to most recombinases, are required for transposition. The first component is the expression of the transposase enzyme and the second is the presence of inverted terminal repeats recognized by the transposase enzyme. The major difference between recombinases and transposases is that transposition occurs at random sites in the genome making it amenable to mutational analysis. Furthermore, the transposons can be induced to excise again to obtain revertants or "gain of function". This is useful information to establish a function of the mutated gene.

In the present invention, transposon inverted repeats, such as the Ds elements, may be placed flanking the landing pad construct but inside the T-DNA borders. Transformation with Agrobacterium will introduce this construct into the host genome. The transposase enzyme is then introduced transiently via techniques such as bombardment, electroporation or viral delivery, or stably via transformation or crossing to plants already expressing the transposase. This would cause the construct to be translocated to other random loci within the genome where secondary mutations and reporter gene expression profiles may be screened. Some transposon systems, such as Ac/Ds, tend to translocate to linked genomic loci, whereas others such as Mu, tend to translocate throughout the genome. Each has their own advantages, disadvantages and utilities for generation of mutants and expression patterns. Transposon systems that randomly translocate throughout the entire genome are desired when the goal is to saturate the genome with insertions. Transposon systems that favor insertion at linked locations are desirable when the goal is to characterize a locus or linked genes.

Plasmid or cosmid sequences may be incorporated into the genetic element trapping or landing pad vectors to allow "plasmid rescue" of interesting and useful genomic loci containing genetic regulatory elements or genes. A segment of DNA carrying an origin of replication and selectable marker functional in bacteria is placed internally within the construct.

Plant transformation: Any method of transferring and integrating a DNA molecule into the plant host genome is useful for this technology. Transformation methods yielding large numbers of independent transformants are preferred. This creates a large library of random insertions to screen and analyze. Methods such as *Arabidopsis* vacuum-infiltration or dipping are well suited for this since many plants can be transformed in a small space, yielding a large amount of seed to screen for transformants. The efficiency of transformation and amount of labor involved are also an advantage for this technique. Agrobacterium is preferred because it tends to yield transgenic plants with single or low copy insertions. This is critical for the analysis of marker gene expression, as well as, analysis of knockout mutants. Also, Agrobacterium typically transfers a linear DNA fragment (T-DNA) with defined ends (T-DNA borders). This is important because the desired product is an insertion that creates an mRNA fusion product. Direct DNA transformation, such as microinjection, chemical treatment, or microprojectile bombardment, are also useful but tend to yield high copy number insertions and undefined termini of the insert.

In the case of Arabidopsis in planta transformation, Agrobacterium-treated plants are grown to maturity and the seed harvested. To obtain transformants, the harvested seed is then germinated under selection pressure (antibiotics, herbicides, or selective growth conditions). When herbicide resistance is used, seeds can be germinated in bulk flats without selection and simply sprayed with the herbicide at an appropriate growth stage.

Most other transformation techniques require a tissue culture stage where transformed cells are induced to regenerate on a medium appropriate for the species being transformed. To distinguish transformed tissue, the regeneration process typically includes selection pressure. This is the most common form of plant transformation for most species but is time-consuming and laborious to obtain hundreds or thousands of independent transformants.

Tagged plant analysis: The reporter gene can be used to monitor the profile of the locus, including quantitative, developmental, inducible, and tissue specific expression. Reporter genes such as luciferase, Renilla luciferase and various versions of GFP are especially useful since their expression can be monitored directly using chemiluminescent or fluorescence and analysis is non-destructive. The expression may be monitored for a functional product using low light imaging equipment or quantitated in extracts using fluorometers. Expression can also be analyzed at the transcriptional level using RT-PCR or Northern analysis. Useful tagged plants are further analyzed for gene copy number with PCR or Southern analysis and genomic location by one or more of several techniques including hybridization based RFLP (restriction fragment length polymorphisms) or in situ hybridization, PCR based AFLP (amplified fragment length polymorphisms), RAPD (random amplified polymorphic DNA), SSR (simple sequence repeats) or CAPS (cleaved amplified polymorphic sequences), or traditional breeding methods. Useful genetic regulatory elements identified by the genomic locus tagging vectors can be isolated for further analysis and other applications. Techniques such as plasmid rescue and inverse PCR may be used to isolate the surrounding genomic sequences for further analysis.

Genomic Landing Pads

The availability of well-characterized promoters and other regulatory elements displaying desirable quantity and characteristics such as temporal and spatial expression patterns is limiting. Additional complexities in gene expression are seen in plant transformation due to the random nature of genomic insertions, position effects and expression stability. Even with the best-studied promoter elements, the activity of ectopic promoters driving transgenes is influenced by the sequences and chromatin structure of the genomic location in which they are placed in the host genome (position effects). These influences cause variation in expression levels and profiles from one independent transformant to another. This variation can range from very high expression to complete lack of expression of the transgene and can also affect the long-term stability of gene expression. This problem is generally overcome by screening large numbers of transformants to identify a few that show acceptable levels, patterns and stability of expression. Gene silencing (loss of expression) is also a problem as these "best performing" plants are advanced through numerous generations and the transgene expression is abolished.

Figure 3:
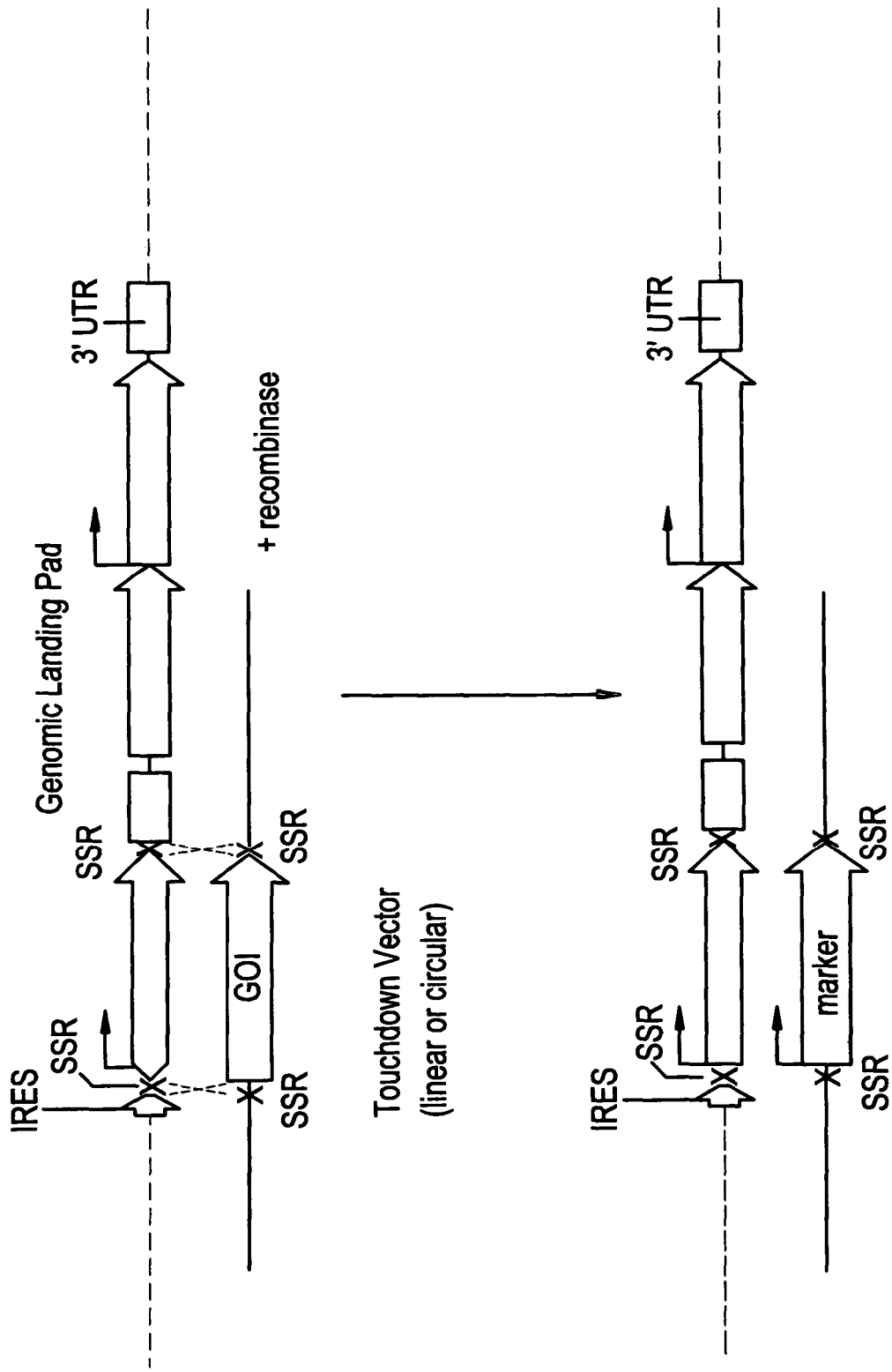
FIG. 3 is a schematic diagram depicting the constructs designed for cloning any GOI in order to incorporate into the "landing pad" by replacing reporter gene (and selectable marker).
Figure 5:
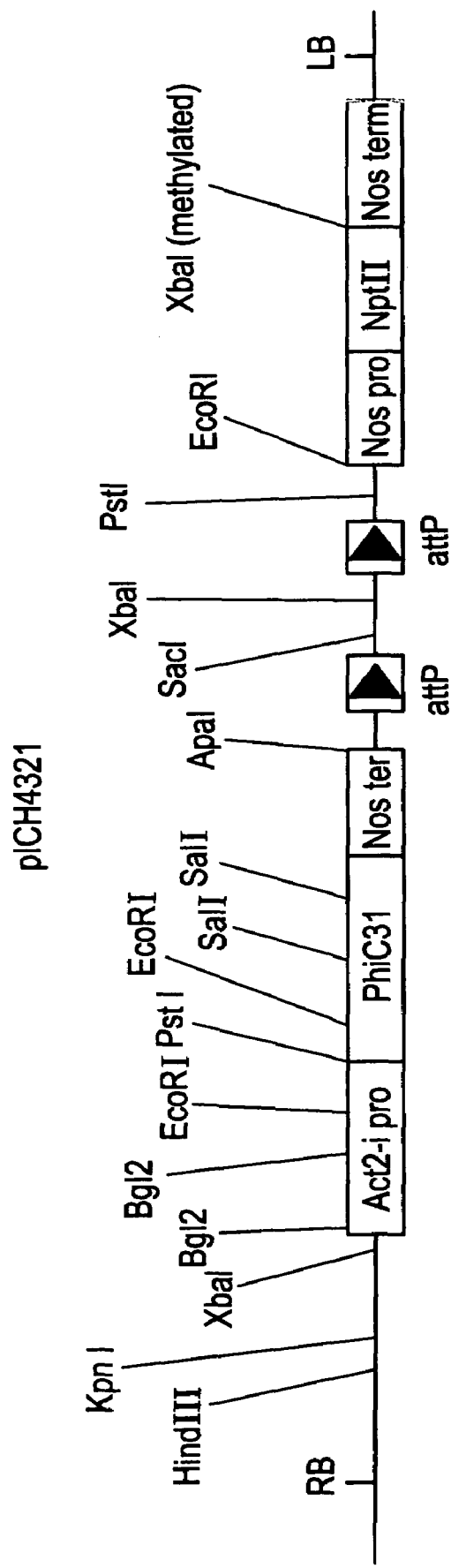
FIG. 5 is a schematic diagram of plasmid pICH4321 (wherein "RB" and "LB" are right and left borders of T-DNA).

One way to alleviate these problems is to insert the transgene of interest into a precise, well-characterized genomic location that gives the desired expression pattern and level depending on the endogenous regulatory elements of the locus rather than using ectopic transcriptional regulatory elements. This targeting is accomplished by combining the genomic locus tagging technology of the present invention along with site-specific recombination to produce "landing pads". Any gene or DNA sequence of interest (GOI) can be inserted into the transgenic "landing pad". A library of transgenic plants containing "genomic landing pad" loci having various temporal and spatial expression patterns based on analysis of the marker gene may be created. Site-specific recombination is then used to incorporate a new GOI into the landing pad thereby placing the GOI under the transcriptional control of this locus. A constructs designed for cloning any GOI in order to incorporate into the "landing pad" by replacing reporter gene (and selectable marker) are shown in FIGS. 3 and 5. In this case any new GOI shall be cloned between two attP sites in the right orientation. Since the new gene is inserted into the same location, the expression is similar or identical to the reporter gene including quantitative, spatial and temporal regulation without the disadvantages of position effects and homology dependent gene silencing.

Figure 4:
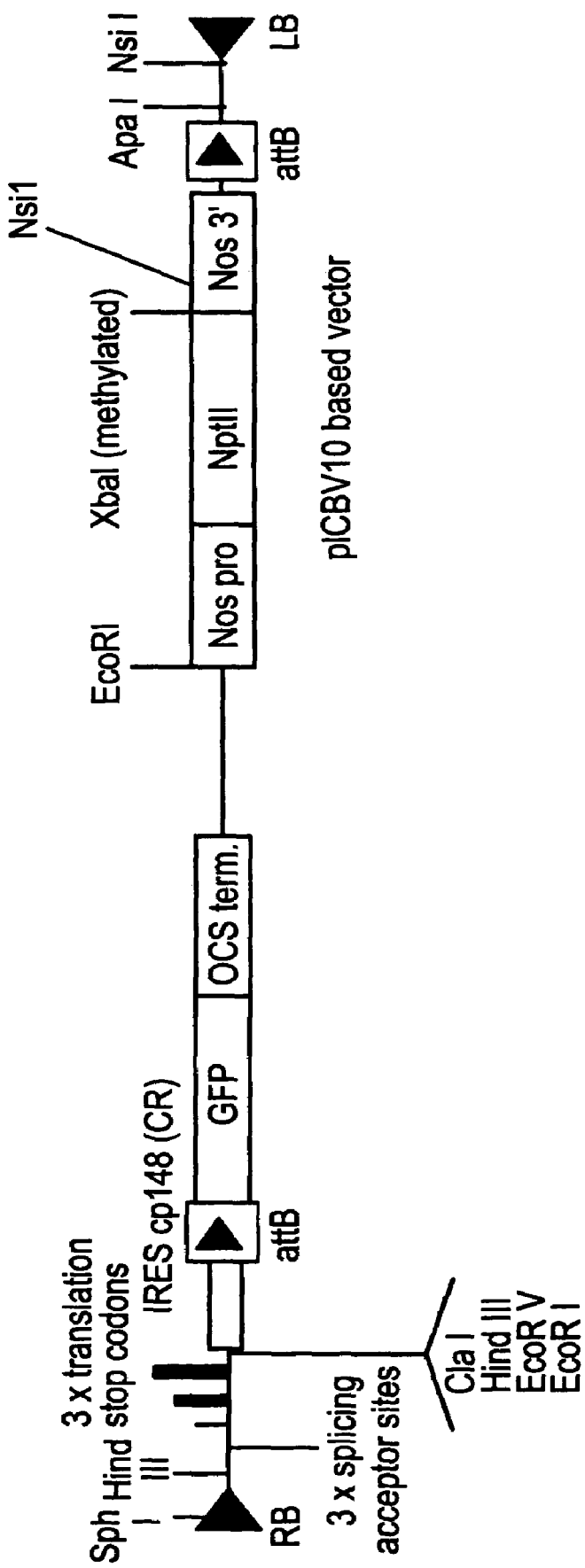
FIG. 4 is a schematic diagram depicting the structure of a T-DNA region of binary vector pICH-LPG.
Figure 6:
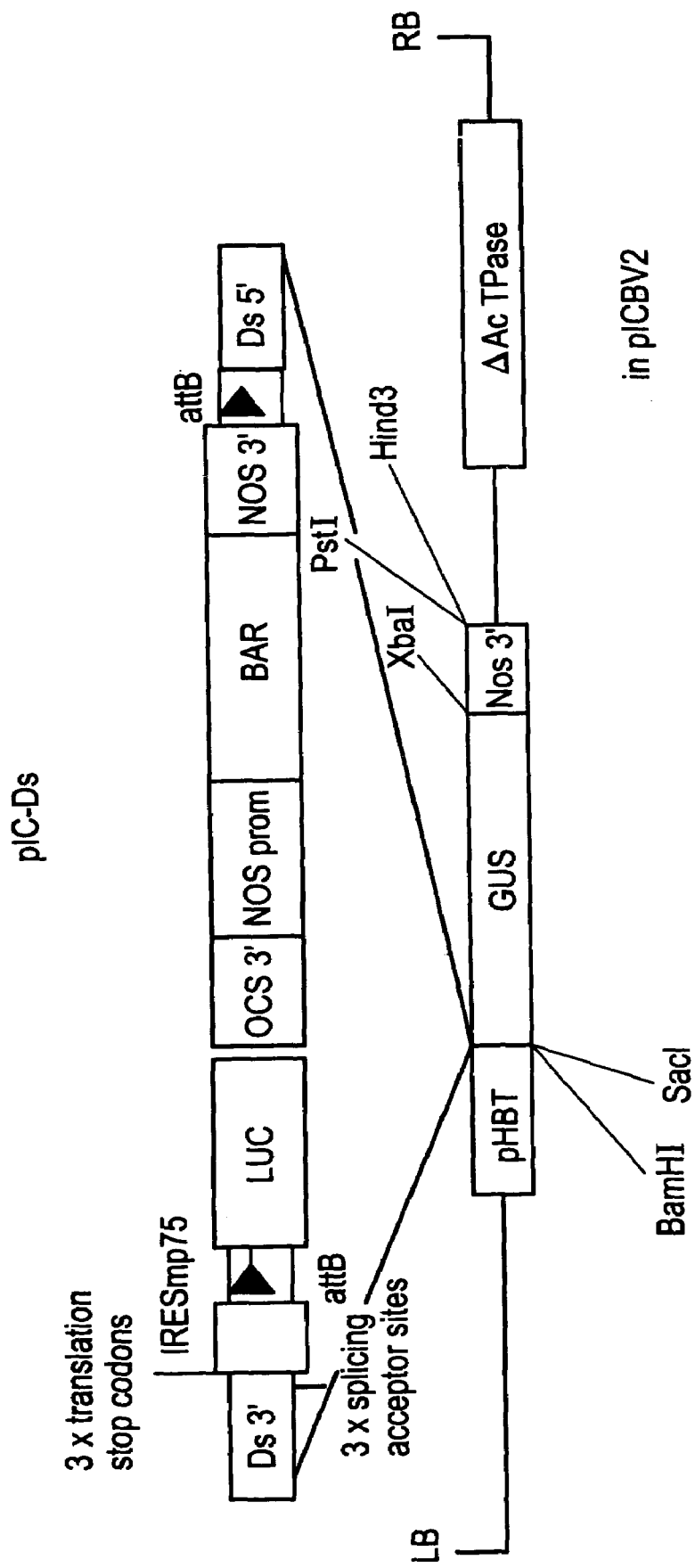
FIG. 6 is a schematic diagram of plasmid pIC-Ds.

Genomic landing pad vectors are essentially the same as genomic locus tagging vectors with the addition of site-specific recombinase recognition sequence(s) (see FIGS. 2, 3, 4 and 6). These sites may be positioned in several locations and orientations to allow insertion of a circular plasmid (FIG. 2) or replacement of the marker gene with the new GOI (FIGS. 3, 4 and 6). For example, single recombination sites may be located upstream of the IRES, between the IRES and marker gene or between the marker gene and 3' UTR. Locating the IRES upstream of the IRES is advantageous because the recombination sequence is not located between the IRES and coding region of the marker where the site-specific recombination site may have an effect on translation initiation. By locating the recombination site downstream of the coding sequence and a touchdown vector containing a recombination site, IRES, and GOI, a polycistronic message capable of expressing both genes is formed. Similarly, for gene replacement, recombination sites may be placed in several locations depending upon the desired outcome, including replacement of the marker gene and/or the selectable marker gene (examples are given in FIGS. 2 and 3).

Plant transformation with genomic landing pad vectors and analysis of transformants are carried out as for the genomic locus tagging vectors described above. Once genomic loci with the desired expression characteristics have been identified and analyzed, new GOIs on a touchdown vector may be introduced via insertion or replacement. Touchdown vectors are vector (e.g., plasmid) constructs carrying the GOI and appropriate elements for incorporation into a genomic landing pad. Like the landing pad vectors, the touchdown vectors contain no transcriptional regulatory sequences, relying upon the regulatory sequences at the site of genomic insertion for transcriptional expression. The configuration of the recombination sites in the touchdown vector must match the sites in the landing pad for the given application including recombination sequence, placement within the construct, orientation and topology of the DNA. For example, the touchdown vector should be in a closed circular form for insertion to occur—other configurations are used to bring about gene replacement or excision.

Transgenic plants tagged with a landing pad vector and displaying the desired characteristics (including arrangement, location and copy number) are then used to insert a touchdown vector carrying a new GOI and appropriate recombination sites. Although not required, the touchdown vector may contain a second selectable marker driven by an independent ectopic promoter allowing for selection of stable integration of the touchdown vector.

For introduction of the desired sequence to occur at the site-specific recombination site within the genomic landing pad, the touchdown vector and recombinase enzyme must be present in the same plant cell carrying the landing pad. Delivery of the touchdown vector and recombinase may occur stably or transiently by any of the methods previously mentioned. However, for insertion, the touchdown vector must be circular making direct-transfer of plasmid the preferred technique. Integration via ΦC31 integrase is preferred because the mechanism of this recombinase is irreversible and stable. Segregation or elimination of the recombinase enzyme is not a critical issue as is the case with most other recombination systems. This allows greater flexibility in the choice of techniques used for delivery and expression of the enzyme.

Depending upon the configuration of the genomic landing pad and the touchdown vector, recombinant plants can be selected by the loss of the reporter gene or loss of the reporter and selectable marker and the gain of the GOI expression with or without a second selectable marker. Plants can be further analyzed for expression of the GOI by Northern or RT-PCR analysis of mRNA levels and ELISA, Western blots or functional biochemical assays. Further molecular data, such as Southerns, PCR or marker assisted breeding techniques may be desirable to verify the proper insertion/replacement has occurred rather than a random integration.

Advantages

Genomic locus tagging vectors: The IRES-based genomic locus tagging vectors are useful to identify promoters and other transcriptional regulatory elements. When using this invention for functional genomics, the expression of the reporter gene is indicative of the vector landing in a functional gene. The expression profile of the reporter gene can be linked to the loss of function due to the insertional mutation within the structural gene.

The IRES element constructs improve upon current versions of gene tagging and promoter- or enhancer-based trapping because expression of the introduced gene is reading-frame independent, eliminating fusion protein products and increasing the number of insertions yielding expression and functional products.

Genomic landing pad: By including site-specific recombination sites it is possible to use the tagged genetic loci as "landing pads" (recipient loci) for the insertion of new genes of interest (GOI). The GOI is constructed in such a manner as to have cognate recombination sites so that it may be effectively inserted into a landing pad locus where it will be under the host cell's transcriptional regulation for that particular genetic locus. The GOI may be placed in numerous host lines having landing pads of diverse expression profiles. This technology is useful for the production of transgenic plants, as well as functional genomics. In order to elucidate the unknown function of a gene it can also be useful to insert gene-encoding regions into numerous landing pad loci, in both sense and antisense configurations, to determine the effect of various ectopic expression patterns, as well as, up and down regulation of the gene.

The genomic landing pad technology reduces the need for transcriptional regulatory elements, reducing the overall size of the vectors and eliminating the requirement for an extensive library of isolated and characterized regulatory elements. The fact that the locus remains in its native environment and genomic sequences are not duplicated eliminates potential position effects and homology dependent gene silencing. The end result is that transgenic plant production is much more precise and efficient with greater control over gene expression levels, patterns and stability.

Plants containing the landing pads described herein can also be used for functional genomics. In general, gene function is most often defined by understanding the effects of mutations of a certain gene. In this regard, the mutations generated in the vast majority of cases are either chemically induced, radiation-induced or by insertional mutagenesis. Often, the outcome of these events is the loss of function of the gene and the effects that ensue. However, it is also possible to define the function of gene by gain of function. That is to say, an observation is made as to what happens to the system (plant) when a gene (endogenous or heterologous) is expressed at a time or a place when it is not normally expressed. Because of the many logistical limitations to plant transformation this approach has not been routinely applied to the discovery of gene function for large samples of genes with the possible exception of using viral delivery methods which also can suffer limitations since it is not possible to express the exogenous gene of interest in all tissues based on a viral delivery system. The Landing Pad system offers significant advantages to other positive expression systems because it achieves both variation in spatial and temporal expression (limited only by the number of unique landing pad lines chosen for the study) and precision of integration in the transformation process.

To define the function or utility for unknown genes, the landing pad lines can be used as recipients to permit analysis of the effect of various expression patterns of the genes of unknown function. For example, it is possible to maintain a stock of landing pad plants having distinct temporal and spatial expression patterns (root, root hair, root tip, meristem, leaf, leaf margin, leaf vein, stem, flower petal, anthers, pollen, ovum, seed, embryo etc.). The experimental genes are cloned in such a manner to include the appropriate site-specific recombination site and are then inserted into each discreet landing pad expression line. Because the site-specific recombination sites and the recombinase direct the insertion to a specific location rather than the random insertions typical of plant transformation, many fewer transformation events per line need to be produced for study. Phenotypic observations may be performed to identify genes, which when expressed ectopically cause changes in morphological features of the plant. Such a result would focus attention on various hormone or growth regulatory functions of the gene. Similarly, agronomic or analytical screens could be implemented, even on large scale, to measure specific traits (oil content or type, altered amino acid or starch profiles, etc.) or qualities (early germination, salt, drought, disease tolerance etc.) that may be affected by the expression of the newly introduced gene. Transformed plants, plant parts, plant cells and protoplasts produced by these processes, and seeds derived from the transformed plants, are prepared in accordance with standard techniques.

The methods of the present invention are applicable to all plants particularly flowering plants, monocots and dicots alike, and crop plants such as cereal crop plants.

The invention will be further described by reference to the following experimental work. This section is provided for the purpose of illustration only, and is not intended to be limiting unless otherwise specified.

EXAMPLE 1

Constructs Design

Figure 7:
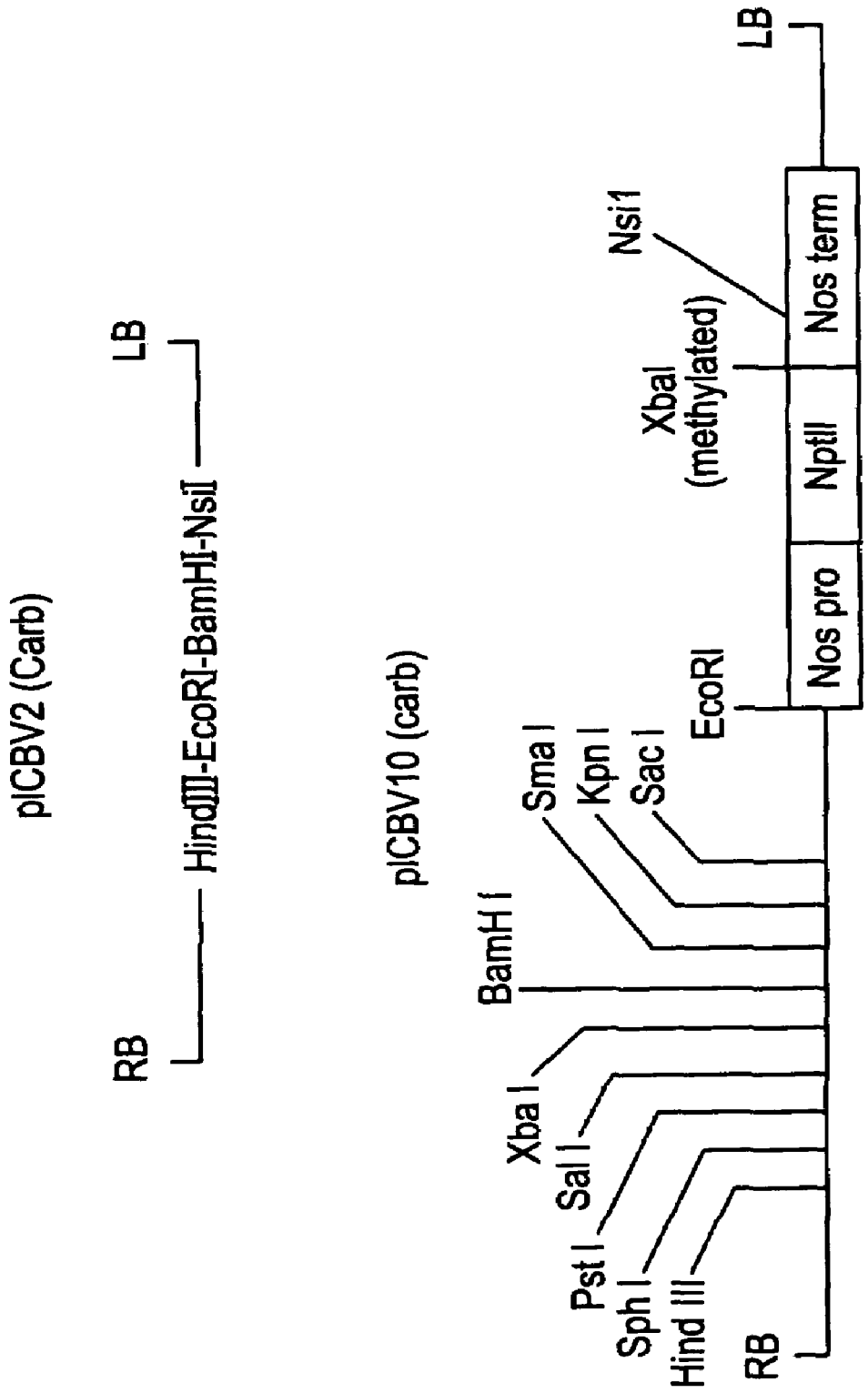
FIG. 7 is a schematic diagram depicting binary vectors pICBV2 and pICBV10.

Series of IRES-mediated expression vectors were constructed using standard molecular biology techniques (Maniatis et al., *Molecular cloning: a Laboratory Manual*. Cold Spring Harbor Laboratory, New York (1982)). All constructs were built on the basis of proprietary binary vectors family pICBV (pICBV2; pICBV10, see FIG. 7). Schematic presentations of the constructs used in this invention are shown in FIGS. 4-6. The sequences and information concerning all the genes and structural elements used in the invention are available from the series of publications and publicly accessible databases. Integrase PhiC31 and its target sites attP/attB (Thomason et al., Mol Genet Genomics 265,1031-8; WO0107572 (2001)). The construct shown in FIG. 5 is designed for cloning of any sequence of interest using Sac1-Xba1 restriction sites placed between two attP sites, thus creating "touchdown" vector with any sequences of interest to be targeted to "landing pad" site. Different Ac/Ds systems and the construct designs are widely described in many publications (Bancroft et al., Genetics 134:1221-9 (1993); Sundaresan et al., Genes Dev. (1995) 9, 1797-810; Meissner et al., Plant J., 2000, 22, 265-74). Δ Ac ("Delta Ac") or stabilized Ac used in this invention was made as described by Bancroft et al., Mol Gen Genet. 233:449-61 (1992). The constructs design can be easily reproduced and diversified by those familiar with the art, based on the description of this invention as well as the information available from the referred publications, especially from the field of "gene trapping" technologies.

EXAMPLE 2

Plant Transformation

In Planta Transformation of *Arabidopsis thaliana*

The plasmids (carbanicillin-resistant) were immobilized into *Agrobacterium tumefaciens* (strain GV 2260) by electroporation. The bacterial cells were grown in 300 ml 2YT media with antibiotics, collected by centrifugation and resuspended in 5% sucrose to $OD_{600}$=0.8.

*A. thaliana* plants were grown until flowering. Then flowering bolts of Arabidopsis plants were dipped in Agrobacterium solution under vacuum applied for a few seconds. Transformed plants were kept in a dark place for 24 hours at high humidity and than transferred into the greenhouse. In the case of BAR gene as selectable marker, the seeds were collected 3-4 weeks later, sowed in soil and sprayed with 100 mg/L phosphinothricin, 0.01% Silvet. The treatment was repeated 2-3 times depending on the efficiency of selection and the frequency of late germination events. In the case of NPTII as selectable marker, the harvested seeds were sterilized and screened for transformants on GM+1% glucose medium (Valvekens et al., Proc. Natl. Acad. Sci. USA, 85:5536-5540 (1988) containing 50 mg $L^{-1}$ kanamycin.

*Brassica napus* transformation.

*Brassica napus* (cv. Westar) hypocotyls transformation and regneration of transformants were performed as previously described (Radke et al., Theor. Appl. Genet. 75:685-694 (1988)).

EXAMPLE 3

Selection for Expression Profiles

Primary transformants of *Arabidopsis* and *Brassica* were directly used for studying the reporter gene expression pattern in the case of T-DNA based "gene trap" construct. For transposon-based "gene trapping", self progeny of primary transformants with the highest transposition frequency (number of GUS+ sectors in the X-gluc stained tissue (Jefferson, Plant Mol. Biol. Rep. 5:387-405 (1987)) were used for screening of the expression profiles of interest. The plants showing tissue-, organ-, developmental, inducible or constitutive expression profiles, but having no GUS-stained sectors (no Ac transposase activity) were selected. The detection of GFP expression profiles were performed under microscope with UV light source (Leica, GFP3 filter) or with the help of transferable UV lamp model B 100 AP (UVP, Upland, Calif., USA). The detection of luciferase (LUC) gene expression was determined with the help of fotometric digital system COOLSNAPHQ-M (Roper Scientific, N.J., USA).

INDUSTRIAL APPLICABILITY

The present invention has applicability in plant sciences such as gene tagging, functional. genomics, plant transformation and breeding.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated as being incorporated by reference herein.

Those skilled in the art will recognize, or be able to ascertain, using no more than routine experimentation, numerous equivalents to the specific substances and procedures described herein. Such equivalents are considered to be within the scope of this invention.

The invention claimed is:

1. A method of introducing a structural gene of interest into plants, comprising:
   (a) providing a plant cell having in its transcribed region a first nucleic acid construct comprising in operable association, at least one tobamovirus IRES (internal ribosome entry site), at least one site-specific recombination site and a reporter gene;
   (b) providing the plant cell of (a) with a site-specific recombinase which recognizes said site-specific recombination site(s) wherein said recombinase is provided recombinantly, and wherein recombinase-recombination site is selected from the group consisting of CRE-lox from bacteriophage PI, FLP-FRT from *Saccharomyces cerevisiae*, R-RS from *Zygosaccharomyces rouxii*, Gin-gix from bacteriophage Mu, integrase/att from bacteriophage Phi C31, and yeast endonuclease I-SceI;
   (c) introducing into the plant cell of (a) a second nucleic acid construct comprising a structural gene of interest flanked by recombination sites such that said structural gene of interest is integrated into the first nucleic acid construct at the site-specific recombination site(s) and wherein said structural gene of interest is under operable control of the IRES, wherein said site-specific recombinase catalyzes integration of the structural gene into the first nucleic acid construct; and
   (d) selecting for plant cells having the structural gene of interest integrated into the first nucleic acid construct, and which is under operable control of the IRES.

2. The method of claim 1 wherein the recombinase is selected from the group consisting of: an integrase from bacteriophage Phi C31, cre-recombinase, flp-recombinase, yeast endonuclease I and R recombinase.

3. The method of claim 1 wherein the structural gene has a known function.

4. The method of claim 1 wherein the function of the structural gene is unknown.

5. The method of claim 1 wherein the first nucleic acid construct comprises one site-specific recombinat ion site.

6. The method of claim 1 wherein the first nucleic acid construct comprises two or more site-specific recombinat ion sites.

7. The method of claim 1 wherein the second nucleic acid construct also comprises a promoter in operable association with a selectable marker gene and a transcription termination region, thus allowing for selection of plant cells with the second nucleic acid.

8. A transgenic plant that expresses the structural gene of interest, prepared by the process of claim 1.

9. A seed obtained from the transgenic plant of claim 8 which contains the structural gene of interest under operable control of said IRES.

10. The method of claim 1, wherein said recombinase is provided in the same vector as the structural gene of interest.

11. The method of claim 1, wherein said recombinase is provided in a different vector than the structural gene of interest.

12. The method of claim 1, wherein said IRES is selected from the group consisting of $IRESMP_{MP75}^{UI}$, $IRES_{MP228}^{CR}$, $IRES_{MP75}^{cr}$ and $IRES_{CP148}^{cr}$.

* * * * *

UNITED STATES PATENT AND TRADEMARK OFFICE
CERTIFICATE OF CORRECTION

PATENT NO. : 7,348,179 B2 Page 1 of 1
APPLICATION NO. : 10/343498
DATED : March 25, 2008
INVENTOR(S) : Yuri Gleba et al.

It is certified that error appears in the above-identified patent and that said Letters Patent is hereby corrected as shown below:

Column 20, line 36 "recombinat ion" should read --recombination--.

Column 20, lines 38-39 "recombinat ion" should read --recombination--.

Column 20 line 57 "IRESMP" should read --IRES--.

Signed and Sealed this

Twenty-sixth Day of May, 2009

JOHN DOLL
*Acting Director of the United States Patent and Trademark Office*